United States Patent
Wessels Wells et al.

(10) Patent No.: US 11,620,750 B2
(45) Date of Patent: Apr. 4, 2023

(54) EMBRYO EVALUATION BASED ON REAL-TIME VIDEO

(71) Applicant: Emgenisys, Inc., Houston, TX (US)

(72) Inventors: Cara Elizabeth Wessels Wells, Dripping Springs, TX (US); Russell Killingsworth, Shamrock, TX (US)

(73) Assignee: Emgenisys, Inc., Houston, TX (US)

( * ) Notice: Subject to any disclaimer, the term of this patent is extended or adjusted under 35 U.S.C. 154(b) by 0 days.

(21) Appl. No.: 17/866,155

(22) Filed: Jul. 15, 2022

(65) Prior Publication Data
US 2022/0351381 A1 Nov. 3, 2022

Related U.S. Application Data

(63) Continuation of application No. PCT/US2021/044423, filed on Aug. 3, 2021.
(Continued)

(51) Int. Cl.
*G06T 7/00* (2017.01)
*G06T 3/40* (2006.01)
(Continued)

(52) U.S. Cl.
CPC ............ *G06T 7/0012* (2013.01); *G06N 3/02* (2013.01); *G06T 3/40* (2013.01); *G06T 7/20* (2013.01);
(Continued)

(58) Field of Classification Search
None
See application file for complete search history.

(56) References Cited

U.S. PATENT DOCUMENTS

| 9,177,192 B2 | 11/2015 | Wang et al. |
| 9,710,696 B2 | 7/2017 | Wang et al. |

(Continued)

FOREIGN PATENT DOCUMENTS

| WO | 2019060911 A1 | 3/2019 |
| WO | 2019191682 A1 | 10/2019 |

(Continued)

OTHER PUBLICATIONS

Lauridsen, Henrik, et al. "Extracting physiological information in experimental biology via Eulerian video magnification." BMC biology 17.1 (2019): 1-26. (Year: 2019).*

(Continued)

*Primary Examiner* — Samah A Beg
(74) *Attorney, Agent, or Firm* — Novak Druce Carroll LLP

(57) ABSTRACT

System, method and computer readable medium that assess characteristics of an embryo by processing video image data of the embryo. Video is obtained, typically from third parties, of a target embryo. The video has frame speed of two frames per second, or faster and includes image data representing morphokinetic movement of the embryo. The image data is processed using a trained machine learning model that assesses embryo characteristics. The video has a duration of ten minutes or less. The assessment can be a prediction of a likelihood the embryo is viable and/or will produce a pregnancy upon transfer into a recipient. Further, the assessment can predict a likelihood the embryo will: (1) produce offspring having a specific sex; (2) embody a genetic anomaly; (3) perpetuate desired traits in produced offspring and/or (4) produce undesired characteristics in produced offspring.

30 Claims, 8 Drawing Sheets

Related U.S. Application Data

(60) Provisional application No. 63/060,554, filed on Aug. 3, 2020.

(51) Int. Cl.
| | |
|---|---|
| *G06T 7/20* | (2017.01) |
| *G06N 3/02* | (2006.01) |
| *G16H 30/20* | (2018.01) |
| *G16H 50/20* | (2018.01) |
| *G16H 50/30* | (2018.01) |
| *G16H 30/40* | (2018.01) |
| *H04N 5/77* | (2006.01) |

(52) U.S. Cl.
CPC ............. *G16H 30/20* (2018.01); *G16H 30/40* (2018.01); *G16H 50/20* (2018.01); *G16H 50/30* (2018.01); *H04N 5/77* (2013.01); *G06T 2207/10016* (2013.01); *G06T 2207/10056* (2013.01); *G06T 2207/20076* (2013.01); *G06T 2207/20081* (2013.01); *G06T 2207/20084* (2013.01); *G06T 2207/30044* (2013.01)

(56) References Cited

U.S. PATENT DOCUMENTS

| | | | |
|---|---|---|---|
| 10,942,170 B2 | 3/2021 | Tan et al. | |
| 11,169,064 B2 | 11/2021 | Prien et al. | |
| 2014/0087415 A1 | 3/2014 | Ramsing et al. | |
| 2015/0260704 A1* | 9/2015 | Bruins | G01N 33/50 435/235.1 |
| 2015/0268227 A1* | 9/2015 | Tan | G06T 7/0016 435/29 |
| 2016/0078272 A1 | 3/2016 | Hammoud | |
| 2016/0078275 A1* | 3/2016 | Wang | G06K 9/6277 382/133 |
| 2018/0256304 A1 | 9/2018 | Sheena | |
| 2019/0024030 A1 | 1/2019 | Wells et al. | |
| 2020/0011883 A1 | 1/2020 | Beim et al. | |
| 2020/0311916 A1 | 10/2020 | Tran | |
| 2021/0249135 A1 | 8/2021 | Rimestad et al. | |
| 2022/0012873 A1* | 1/2022 | Silver | G06N 3/04 |

FOREIGN PATENT DOCUMENTS

| | | |
|---|---|---|
| WO | 2021148961 A1 | 7/2021 |
| WO | 2022031765 A1 | 2/2022 |

OTHER PUBLICATIONS

Nguyen, Tan H., et al. "Gradient light interference microscopy for 3D imaging of unlabeled specimens." Nature communications 8.1 (2017): 1-9. (Year: 2017).*

Kanakasabapathy, Manoj Kumar et al., "Development and Evolution of Inexpensive Automated Deep Learning-Based Imaging Systems for Embryology", Lab Chip 19(24) (2019): 4139-4145; Dec. 21, 2019.

Siva-Rodriguez, Julio et al., "Predicting the Success of Blastocyst Implantation from Morphokinetic Parameters Estimated through CNNs and Sum of Absolute Differences", 2019 27th European Signal Processing Conference (EUSIPCO); IEEE, 2019. (Year: 2019).

International Search Report and Written Opinion; PCT Application No. PCT/US2021/044423; dated Nov. 16, 2021.

* cited by examiner

EMBRYO EVALUATION BASED ON REAL-TIME VIDEO

CROSS REFERENCE TO RELATED APPLICATIONS

The present patent application is a continuation of PCT/US2021/044423 filed Aug. 3, 2021, designating the United States and which claims the benefit of U.S. Provisional Patent Application No. 63/060,554 filed Aug. 3, 2020. Each of the aforementioned patent applications is expressly incorporated herein by reference, in its entirety, without disclaimer.

BACKGROUND

Utilizers of the presently disclosed technology are reproductive endocrinologists, specialized OB/GYN's, embryologists, veterinarians, animal breeders and trained laboratory personal, among others. In the realm of human reproduction, users of this technology are embryology lab directors and clinical embryologists who are practicing Assisted Reproductive Techniques (ART). ART patients, in particular, In Vitro fertilization (IVF) patients are influencers and payers of this technology as they play a significant role in electing to use various technologies on their gametes, oocytes and embryos. Customer interviews were performed with 231 respondents during the 2018 National Science Foundation I-Corps National Atlanta Winter Cohort. The results concluded there has not been any transformative technologies to predict embryo viability in nearly four decades, which is nearly equivalent to the time in which the first IVF baby was born in 1978. Clinical embryologists and trained personnel are responsible for selecting the embryo which gets transferred into the patient and often unknowingly transfers non-viable embryos into patients due to lack of accurate means to evaluate embryo health and quality. Embryologists' reputation is predominantly based on pregnancy success rates and labs and associated physician(s) are competing for high pregnancy outcomes. These success rates are published, therefore impact their reputation, the more positive, the more it enhances their reputation and ability to attract new clients. Initially, the disclosed technology is targeting the United States clinical infertility ART sector but will be aggressively scaled into the growing $37.7 billion global infertility market. This technology is the first and only embryo assessment tool of its class which is non-subjective, non-invasive and allows real time assessment of embryo morphokinetics to deliver immediate user output. The most commonly used method to select the embryo to transfer is by visual examination of the embryo under a light microscope.

Infertility is classified as a disease by the World Health Organization and affects 48.5 million couples worldwide or one in eight couples. In Vitro Fertilization (IVF) is the most effective treatment of infertility, but the 2018 livebirth rate was only 26%. Equally notably, only 57% of women suffering from infertility seek treatment in the United States. IVF is renowned for being expensive, stressful, hopeless and unsuccessful. This is a psychologically painful process for patients who typically feel sensitive to biological and social pressures and feel as if time is against them and they "are not getting any younger" to raise their child. For these reasons, infertility patients do not feel confident in the process and many never receive medical assistance starting their families.

In addition to the value of ARTs as a treatment of infertility, ARTs offer value as a means to preserve fertility though cryopreservation of eggs, sperm and embryos, enable single individuals and homosexual couples to start families. Additionally, ARTs can preserve healthy cells/gametes of cancer patients prior to undergoing chemotherapy allowing them to be used in the future. For these purposes, ARTs are becoming a routine method to start a family.

Since the birth of Louise Brown in 1978, over 10 million babies have been born as result of IVF and Intracytoplasmic Sperm Injection (ICSI) worldwide. In the United States, babies born from IVF/ICSI comprise nearly 2% of the annual birth rate. For this procedure, a woman is given super-ovulatory hormones to encourage more eggs to develop in the ovaries. The woman's follicular development is closely monitored to time the egg retrieval, in which the fertility specialist aspirates the eggs from the ovary. Each egg is fertilized with sperm and the fertilized eggs can develop into embryos and cultured for 5-6 days. It is likely multiple embryos will develop into seemingly healthy blastocysts. The embryologists are responsible for choosing which embryo(s) get transferred into the patient. Any remaining embryos are typically frozen and can be used for subsequent transfer attempts. This process is considered as a "round" of IVF and costs approximately $23,000. If a pregnancy does not occur, the patient can opt to undergo a frozen transfer, in which one of the remaining frozen embryos is thawed and transferred into the patient. Frozen embryos can be transferred until there are no more available embryos, in which case the entire process must start over. On average, patients undergo 2.7 rounds of IVF and spend $60,000 to achieve a pregnancy, which survives to term. A major contributor to the low success rate of IVF is failure to choose healthy, viable embryos for transfer.

In accordance with the present disclosure, assessment is performed on all of the available embryos before the transfer, to better predict embryo health and developmental potential, ultimately reducing the number of transfers needed to achieve a successful pregnancy. This benefits the patients with significant cost and time savings, which also lead to psychological benefits. Direct customers are REI's, clinical embryology lab directors, embryologists and trained laboratory personnel. Fertility clinics nationwide are competing for the highest pregnancy rates, as patients can look up pregnancy data in the Society of Assisted Reproductive Technologies (SART) reports, physician clinic sites and other media outlets and choose to receive treatment by the clinic and specialist of their choice. Indirect users of the technology are the patients undergoing IVF. In most cases, the patient assumes the cost of the procedure, whether or not pregnancy occurs. Many patients pay out of pocket, as infertility treatment is not covered by most insurance plans in the United States. However, there is a growing mandate for fertility coverage. Insurance companies are pushing for the adoption for new technologies to reduce treatment costs. REIs and embryologists oftentimes offer patients a variety of treatment options and elective diagnostic options to allow the patient some flexibility over their reproductive outcomes and treatment budget.

In the United States, 271,398 cycles were performed in 2018. Any technology which enables embryologists to select the healthiest embryos to transfer and which can assist in determining embryo survival of cryopreservation will offer improvement in pregnancy outcomes. Just a 3% improvement in pregnancy outcomes offers over $187 million in savings to patients in the United States annually. Additionally, technologies to improve pregnancy success per transfer will further promote single embryo transfer (rather than multiple embryo transfer) which decreases costs, and most importantly, complications to mother and baby from multiple gestations.

SUMMARY

This innovative technology utilizes video motion magnification to amplify cellular morphokinetics to indicate changes in embryo growth and development, presence of genetic traits, or death and decay in real time. Amplified videos can be used to develop deep learning algorithms for development of an artificial intelligence software package to provide a non-invasive, quantitative, non-subjective method to distinguish high-quality, viable embryos likely to result in a healthy pregnancy. Currently, embryologists have limited ability to evaluate embryo health and viability, making it common practice to unknowingly transfer dead or inviable embryos into patients. This technology will allow the user to make more informed decisions about which embryo(s) to transfer into patients and reduce the transfer of low-quality embryos which DO NOT establish pregnancies. Technologies to improve pregnancy outcomes of IVF improve both the psychological and financial impact of infertility to patients. Another aim of the technology is to enhance the workflow of the embryologist by enabling a multi-embryo scan and immediate feedback through real time analysis. Improving pregnancy outcomes of IVF reduces costs to patients and insurance companies, improves clinic performance, improves embryologist training, and reduces the stress encumbered by fertility patients, embryologists and physicians.

Combining state-of-art artificial intelligence, machine learning, graphic image processing and optics systems, practical insights from clinical embryologists and scientific input from data engineers, the present technology provides the world's most comprehensive embryo evaluation system measuring embryo morphokinetics, viability and development in a single, easy to use system. The technology utilizes video motion magnification which takes a standard video sequence as input, and applies spacial decomposition, followed by temporal filtering to the frames. The resulting signal is then amplified to reveal hidden information. With this technology, the user can examine growth and development and detect the presence of genetic abnormalities. Our deep learning software measures these changes to rank embryos so the embryologist can select to transfer the healthiest embryos into patients with the highest likelihood to survive to term. This technology surpasses the industry gold standard for embryo assessment and requires a fraction of the time and cost.

DETAILED DESCRIPTION

Figure 1:
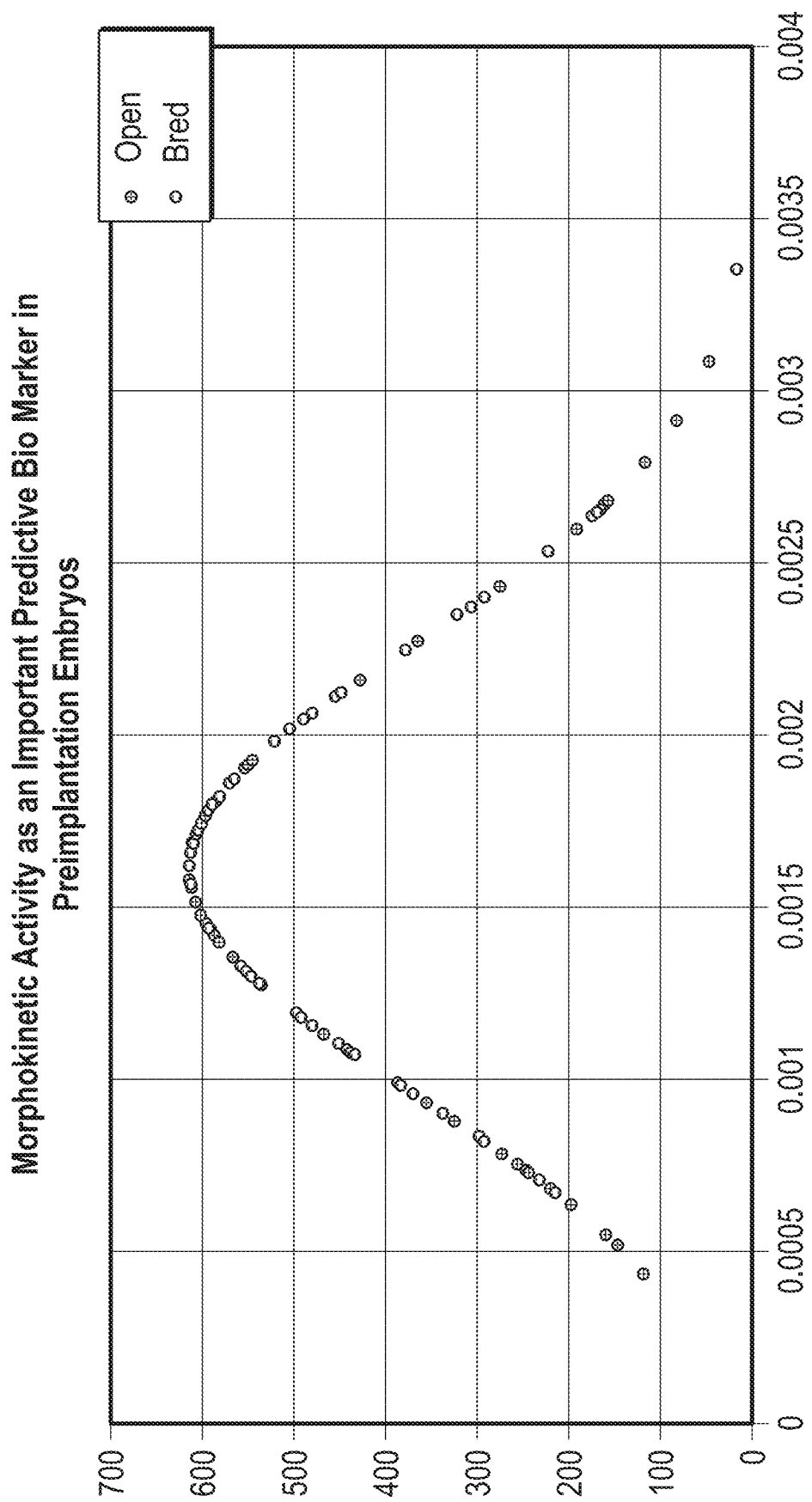
FIG. 1 shows morphokinetic activity as an important predictive bio marker in preimplantation embryos.

The solutions made possible by the present technology have among others, a focus on the $6.2 billion market in the United States human clinical infertility sector. The technology will also scale into the $37.7 billion global infertility market. Statistics state 95% of infertile people do not seek care and technologies to drive down costs and increase success will expand the growth of the infertility market. The market analysis indicates that a 50% reduction in the price of IVF services would translate into a 160% increase in the utilization of fertility services.

Initial customer discovery has been performed using primary market research data collection. Forty-six prospective customer interviews were conducted in the Regional Southwest Node I-Corps cohort. Further customer discovery was conducted during the National I-Corps Node with Award Number 1444045 in Atlanta in January of 2018. 231 customer interviews were conducted in Ga., Calif., Colo., Tex. and Ariz. Customer discovery has continued over 750 interviews have been conducted to date. From these interviews, customer pain points were learned from REI specialists (Reproductive Endocrinology and Infertility physicians), lab directors managing IVF labs, senior embryologists, junior embryologists, fertility nurses, OB/GYN, IVF patients with success stories, IVF patients with failed attempts and current IVF patients. While the market opportunity was validated in the general infertility sector, it was identified that lab directors over-seeing the operations and safety of embryology labs were the direct users and final decision makers about which biomedical devices and diagnostic tools would be used in their clinic(s).

The surveyed data and scientific literature suggests very few changes have been made to the method in which embryos are graded and selected for transfer in nearly four decades, and many technologies promising to increase the pregnancy rate of IVF are successful, but also increase the miscarriage rate so the take-home baby rate has not improved. Shockingly, IVF success rates have declined in recent years and demonstrate negative association with mild stimulation protocols, elective single embryo transfer, preimplantation genetic testing, all freeze cycles, embryo banking and extended culture. The industry uses the annual SART National Summary Report for accurate clinical outcomes, number of cycle starts and break down of live birth rates as classified by treatment type and patient age. Lab directors shared many new imaging technologies exists, such as time lapse imaging, but the equipment is too costly and space consuming for use in routine clinical embryology.

During the survey, lab directors and embryologist expressed that non-invasive technologies which help standardize embryo selection can reduce human error, as it is well known current embryo selection procedures are highly subjective and dependent on embryologist's discretion of the embryo's visual morphological appearance. Additionally, non-invasive technologies to help predict embryo health can enhance the consistency of predictions, allow informed decision making and enhance patient education and expectations. There is a demand to reduce the psychological impact of infertility treatment. Many patients expressed that they feel as if they are running out of time to start their families. They want to be active parents and feel the clock is against them. Many patients have spent years trying for a baby. When they finally decide to seek treatment, they are often put on a waitlist to visit the clinic of their choice. Each failed round of IVF takes precious time. Technologies to reduce the time to pregnancy will alleviate the psychological burden on patients.

It was validated that a readily available market opportunity in the clinical infertility sector exists. There are 448 IVF clinics in the United States, as well as donor egg banks which collaborate with over 150 IVF clinics. The landscape of IVF clinics is rapidly changing. Launched by Prelude Fertility, "the $200 million start-up" which incorporated many clinics nationwide offers IVF treatment to patients, as well as encourages young women to freeze their eggs to preserve their fertility. Prelude is regarded as the "nation's fastest growing network of fertility clinics and the largest provider of comprehensive fertility services." Prelude aims to lower the up-front cost of fertility treatment. Other national brands are following suit to help standardize the fertility industry, opening up opportunities for technologies to help improve the quality and consistency of their services and patient experience. Through this customer discovery journey, it was affirmed that a subscription to lease the software and to sell a compatible consumable is the most scalable and sustainable revenue model to capture revenue based on test.

The embryo screening technology market is limited by the requirement that embryos must survive the diagnostic process unharmed. Many existing assessment methods such as staining, electron microscopy, and genetic testing are only used in a research setting because the processes are lethal. The most commonly used method to assess the quality of embryos and oocytes is a morphological analysis through a light microscope. In this assessment, the technician examines the cells for visually apparent characteristics such as cell shape, size, symmetry, color and rate of development. While this method is noninvasive and cost effective, it is subjective and relies solely on the examiners discretion and does not include information of an embryo's biochemical content or genetic make-up. To advance the morphological analysis, time lapse imaging systems, such as the EmbryoScope®, are available to allow monitored controlled culture to link developmental events and specific time points. In a survey published in the Journal of Reproduction and Genetics, only 17% of surveyed labs had a time lapse imagining system and the majority of surveyed lab directors claim "time lapse imaging will not become the standard of care because the technology is too expensive, there is no evidence it provides additional benefit and it is too time intensive and impractical." Others said that the only benefit of time lapse imaging is that it provides undisturbed culture.

The fertility world is starting to incorporate technology utilizing artificial intelligence into their laboratory systems. These systems are typically a function of time lapse imaging or computer analysis of still images. Most notably, a start-up company called Life Whisperer has been making headway for embryo artificial intelligence analysis. Life Whisperer is an Australian company, which processes 2D static images of embryos through the system for analysis on embryo morphological characteristics. According to studies performed in conjunction with Ovation Fertility, Life Whisperer AI technology showed 50% improvement in prediction for successful implantation. Other companies are also using artificial intelligence for embryo selection. However, the present technology is unique and distinct, as it incorporates artificial intelligence to analyze amplified embryo morphokinetics, movement and change in video systems, rather than cell morphology from static or time-lapse imaging.

Methods of genetic assessment involve the biopsy of cells from the embryo. The biopsied cells are then sent off to an off-site lab for genetic testing and the remaining embryo must be frozen until lab results are received. Pre-Implantation Genetic Testing (PGT) encompasses both Pre-Implantation Genetic Screening and Pre-Implantation Genetics Diagnosis, which can inform embryologists and patients of genetic abnormalities (such as aneuploidy or trisomy), genetic diseases and embryo sex. PGT was designed for high-risk patients with known condition or genetic trait, and not for the average IVF/ART patient. Disadvantages of PGT are a result of the invasive nature of the test, which increases risk for cell death, requirement of expensive equipment and highly trained personnel and expensive costs ranging from $4000-$7500 on top of the fees associated with IVF. PGT data suggest there is no difference in pregnancy rate on patients under the age of 36. Other reports claim PGT significantly increases pregnancy outcomes, but many physicians warn that it also increases the miscarriages, indicating the take home baby rate has not improved. The noninvasive embryo analysis system of the present disclosure can be used as a standard of care in a laboratory protocol.

A competitive advantage of the present technology is it is non-invasive, non-subjective, utilizes a quantitative analysis incorporating artificial intelligence and deep learning algorithms, evaluates embryo growth and development in real time and offers immediate feedback to users at an affordable price to clinicians, labs and patients. The technology does not subject the embryo to any unnecessary risks, does not require biopsy of cells or manipulation, allows scanning of multiple embryos at once resulting in predictive data in less than 2 minutes. With the technology, the user can see changes in embryo morphokinetics in real time. Preliminary data has been collected on 150 bovine embryos. Significant changes in embryo morphokinetics, movement, growth and development in real time were observed. This technology is anticipated to have rapid success in the marketplace, as it is a safe and effective means to analyze in real time embryo health which is an advancement to current techniques.

Regarding morphokinetic activity, reference is made to FIG. 1 in which the mean of average subzonal changes were determined to represent embryo movement or morphokinetic activity. The figure was divided by mass area to represent percent (%) movement to standardize embryo morphokinetic activity per individual embryo. The percent (%) morphokinetic activity was ranked and plotted for 94 bovine embryos (n=94). 24 embryos (25%) had morphokinetic changes outside of 2 standard deviations from the mean, which is demonstrated on the left and right tails of the scatterplot. Of these 24 embryos, 17 embryos did not establish pregnancies (70%). These 17 embryos represent 18% of the total 94 embryos. In nature, it is found that 20% of grade 1 and 2 embryos are incompetent at time of transfer. Data from this study suggests embryos outside of 2 standard deviations of the mean can represent these incompetent embryos, thus suggesting this technology is effective at predicting embryo competency of embryos in in vitro culture.

Figure 2:
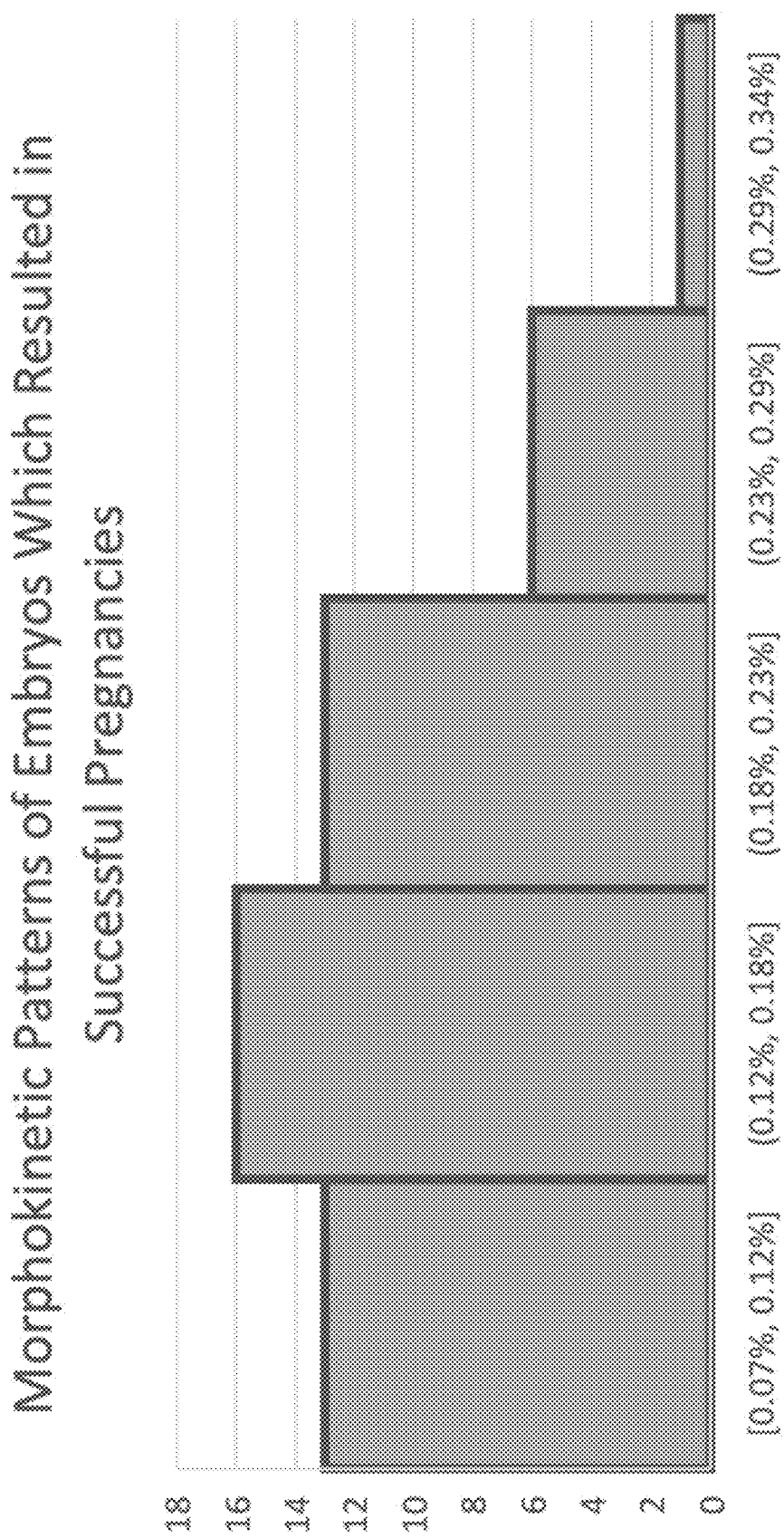
FIG. 2 depicts morphokinetic patterns of embryos that resulted in successful pregnancies.

FIG. 2 depicts morphokinetic patterns of embryos that resulted in successful pregnancies. Therein, the mean of average subzonal changes were determined to represent embryo movement or morphokinetic activity. The figure is divided by mass area to represent percent (%) movement to standardize embryo morphokinetic activity per individual embryo. The percent (%) morphokinetic activity was ranked and graphed for 94 bovine embryos (n=94) on a histogram. 50 embryos in this study resulted in pregnancy. Of these 50 embryos, 42 embryos (84%) demonstrated morphokinetic activity (percent, %) from 0.07%-0.23%. Number of embryos demonstrating percent morphokinetic activity from 0.07%-0.12%, 0.12%-0.18% and 0.18%-0.23% were not statistically significant (p>0.05). 6 embryos (12% of embryos which established pregnancies) demonstrated percent morphokinetic activity 0.23%-0.29% and 1 embryo (2%) demonstrated percent morphokinetic activity 0.29-0.34%. Number of embryos which these percent morphokinetic changes were significantly less than embryos with less morphokinetic activity.

Figure 3:
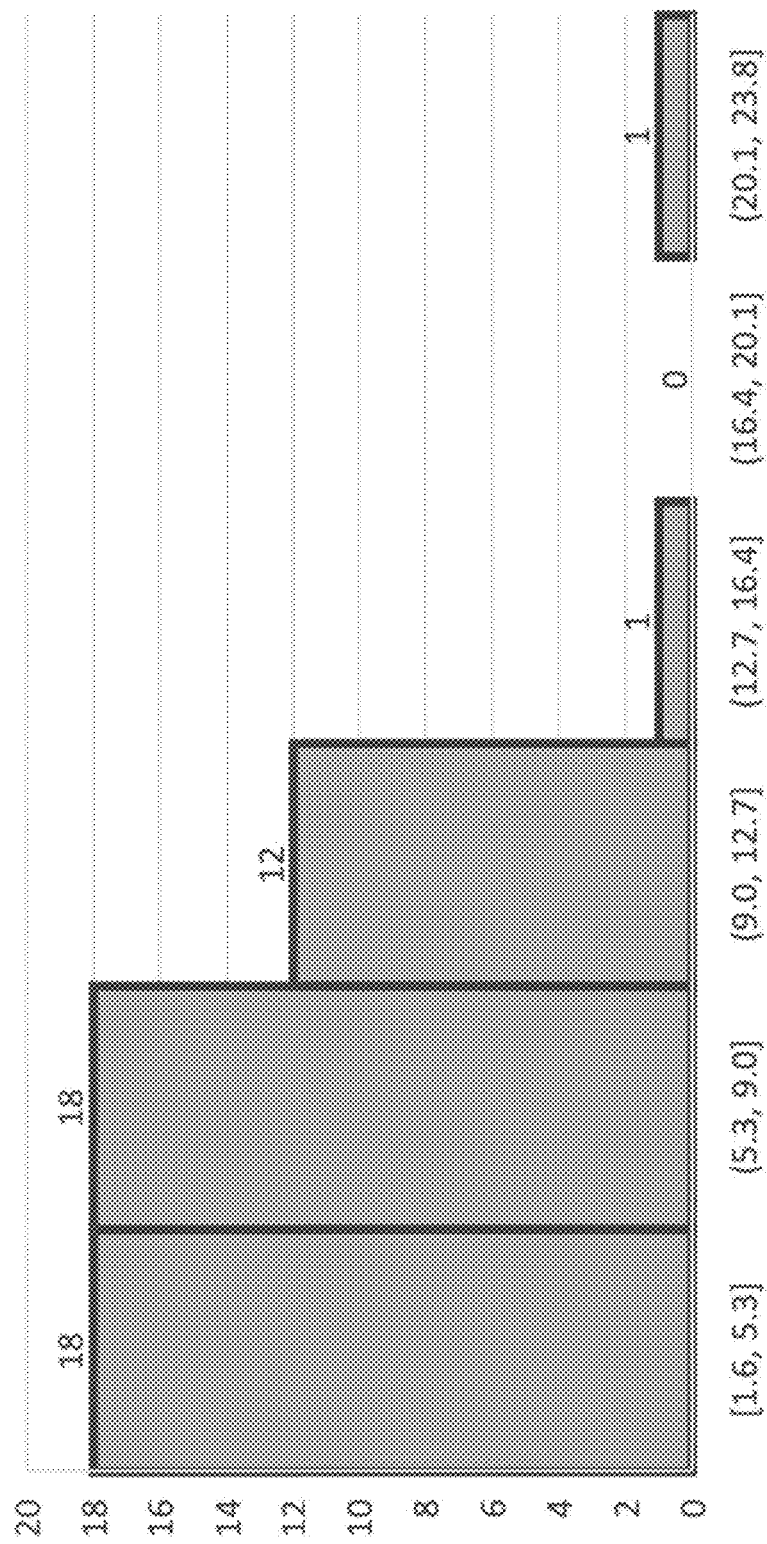
FIG. 3 depicts the range of embryo movement within subzonal space is an important indicator of embryo competency.

FIG. 3 reflects the range of embryo movement within subzonal space is an important indicator of embryo competency. Therein, the distance between the outer contours of the mass area and zona pellucida were measured at specific locations at 5 second intervals during a 35 second observatory period. The range of each distance was calculated over the 35 second duration and averaged for all 12 specific locations for all 94 embryos (n=94) which were transferred into recipients. Embryos with a lower range in subzonal activity established pregnancies at a higher rate than embryos with a high range of subzonal activity (P<0.05). 48 out of 50 embryos (96%) demonstrated a range of motion 1.6 um to 12.7 um, whereas only 2 embryos (4%) demonstrated a range of motion in the subzonal space higher than 12.7 um.

Figure 4:
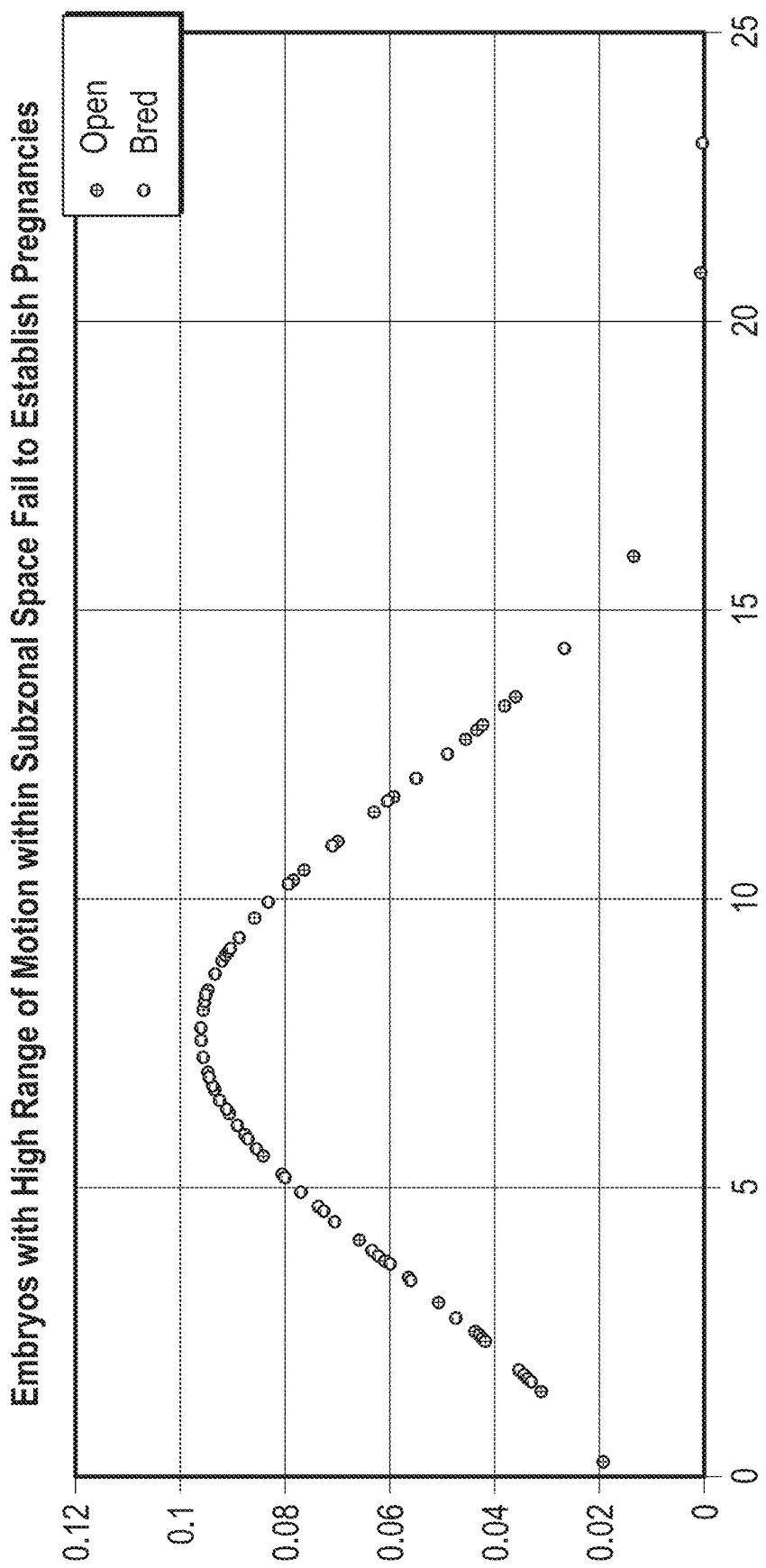
FIG. 4 depicts the distance between the outer contours of the mass area and zona pellucida were measured.
Figure 5:
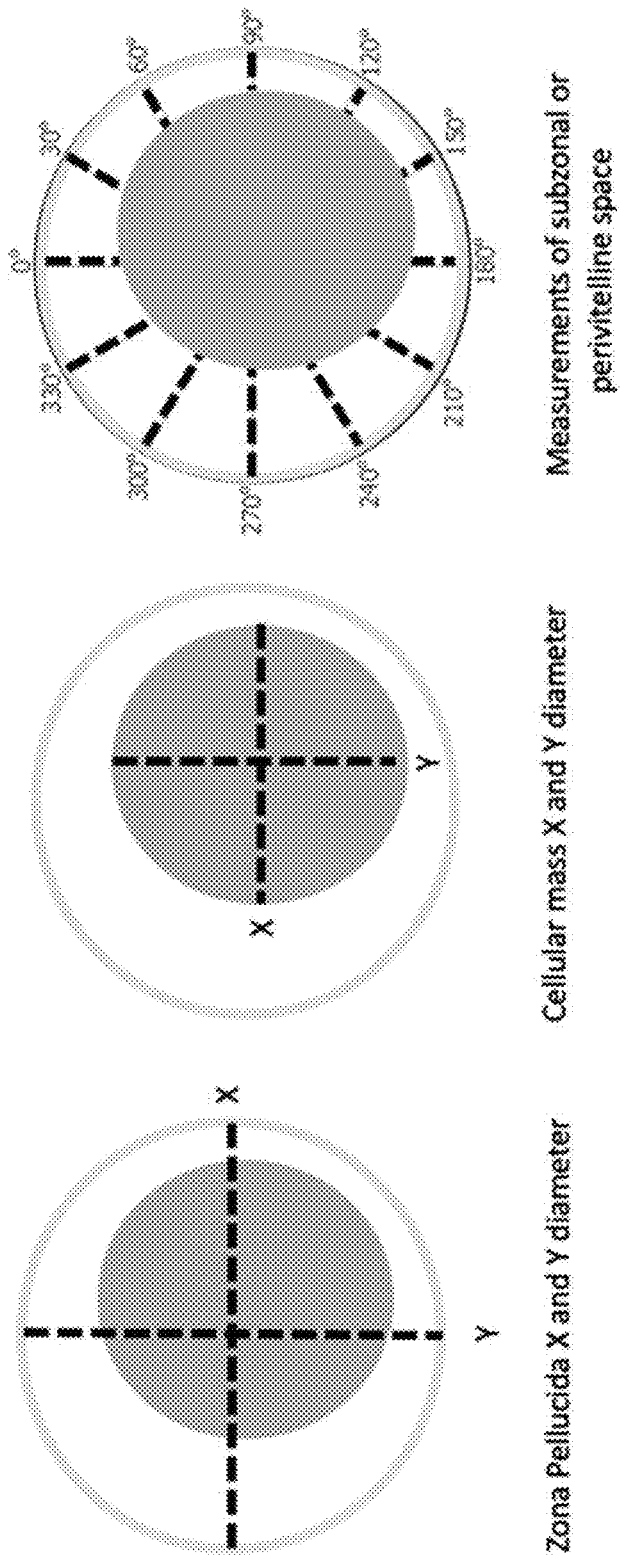
FIG. 5 illustrates components and measurement axis of a blastocyst.
Figure 6:
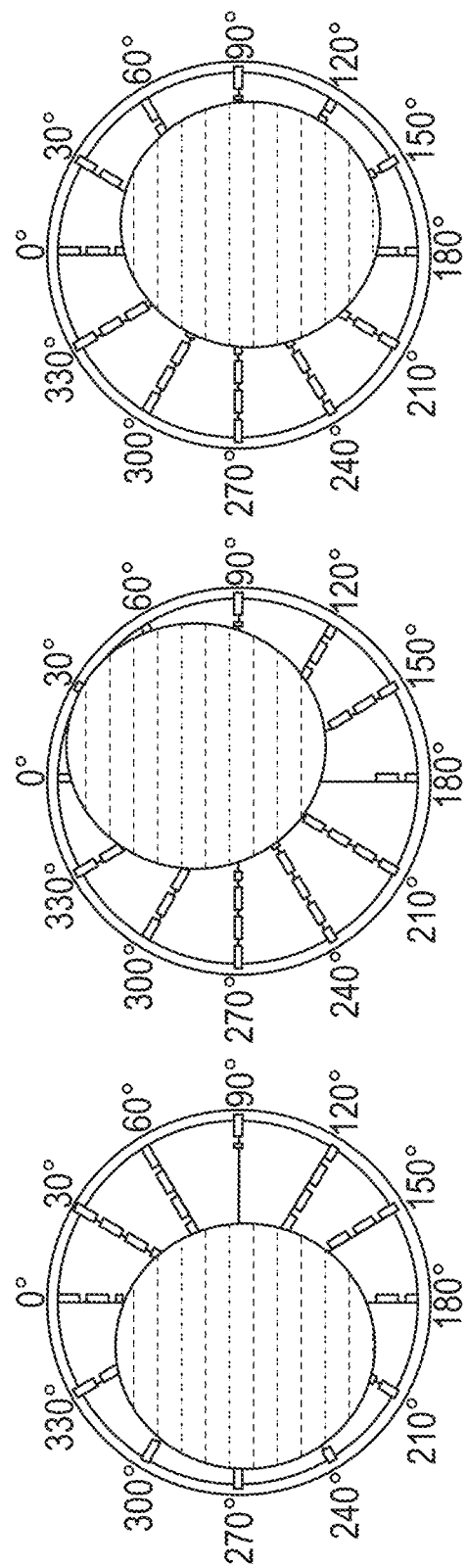
FIG. 6 demonstrates movement of the cellular mass within the pellucida of a blastocyst.

FIG. 4 depicts that the distance between the outer contours of the mass area and zona pellucida were measured at specific locations at 5 second intervals during a 35 second observatory period. The range of each distance was calculated over the 35 second duration and averaged for all 12 specific locations for all 94 embryos (n=94) which were transferred into recipients. 9 embryos (9.57%) demonstrated a range in subzonal activity greater than 12.5 um. 7 of the 9 embryos demonstrating a range greater than 12.5 um did not establish pregnancies, indicating embryos with a high range of subzonal activity in a 35 second time duration are less likely to establish pregnancies than embryos with a more moderate range of motion.

As an enhancement, Video Motion Magnification (VMM) uses a standard video sequence as input, and applies spacial decomposition, followed by temporal filtering to the frames. The resulting signal is then amplified to reveal hidden information. This technology has been utilized in various physiological applications, including remote and non-invasive means to measure heart rate and infant respiration. In essence, this software can take videos of seemingly static images and allow their micro-motions to be visually apparent. As it is well documented, developing embryos are undergoing mitosis at an exponential rate. Originally, it was hypothesized that applying video motion magnification software to embryos could allow one to see embryo development, embryo decay, and detect for the presence of genetic abnormalities. Now it is known that this enabled visualization and the underlying data allows one to find the status of embryo viability immediately prior to transfer utilizing a relatively short, real-time video taken at that time. The duration of the video is short, generally a few minutes or less. Advantageously, the duration can be less than a minute thereby facilitating the technician's workflow. Such technology features allow assessment of embryo health and viability and meets the needs of the clinical embryologist because it enables a multi-embryo scan, is non-invasive and is compatible with standard video equipment. The consumable will be compatible with the optics system to enhance the effectiveness of the graphic image processing, embryo identification and provide consistent revenue generation.

In a pilot study to determine the effectiveness of video motion magnification to amplify previously undetectable embryo morphokinetics, videos of bovine blastocysts were recorded at ×150 magnification for two minutes by a licensed veterinarian with an inverted microscope. Once recorded, videos were filtered with the video motion magnification system platform Lambda Vue (discussed in greater detail below), movement in both the inner cell mass and zona pellucida were visually evident. Protrusions, bulges, depressions, pulses and changes in embryo shape were observed. The present technology became the first in its class to amplify and analyze micro-motions and morphokinetics of embryo growth and development in real time, without the use of time lapse imaging. Using ImageJ software, developed by the National Institute for Health, measurements of the bovine embryos were taken at specific time point to evaluate changes in embryo shape and size over time. These measurements were used to create deep learning algorithms for subsequent software development to utilize video motion magnification to predict embryo health. All grade 1 and 2 embryos which were recorded were transferred into recipients and preliminary pregnancy data was obtained with rectal ultrasound. In this pilot study in the bovine model, preliminary data suggests video magnification software is effective at demonstrating changes in embryo morphokinetics in real time without the use of time lapse imaging and can generate meaningful data to show visual evidence of active embryo growth to suggest viability and genetic competency in short observatory periods.

This present technology provides a comprehensive, portable platform including an inverted optics system, application to host to run video motion magnification, embryo prediction software and an accompanying laboratory one-time use consumable. The consumible will consist of a disposable, polystyrene dish, which is specific and compatible with the machinery. Each consumable will have a unique QR code compatible with provider software. Exemplarily, the dish can consist of 8 pre-labeled wells, to easily place embryos in the field of view, identify, and sort post-results and improve the accuracy of the graphic image processing.

Data derived from the bovine model demonstrates that pre-implantation embryos move and undergo visible physical changes when micro-motions are amplified. Protrusions, bulges, depressions and shifts in the inner cell mass, trophectoderm and zona pellucida have been observed.

Blastomeres are actively dividing, increasing embryo mass until differentiation occurs at the blastocyst stage of development, in which the blastomeres begin to arrange themselves into a distinct inner cell mass (developing fetus) and trophectoderm (developing placenta). The human oocyte develops from a single cell to a blastocyst (~300 cells) in a span of 5-6 days. Slight changes in blastomere arrangement, size, cell count and orientation can be visually observed every few hours under a light microscope and time lapse imaging helps document these changes. Despite the fact embryology experts realize the embryo is constantly growing and evolving, it is not possible to see real time microscopic changes under most microscopy systems.

It is also well documented dying cells undergo physical changes as well. When a cell dies, membrane proteins lose structural integrity and cannot osmo-regulate their intracellular environment. Constituents from the external environment permeate into the cell through osmosis and intracellular constituents leak out of the cell. It has been observed that non-viable embryos acutely absorb water as equilibrium is attempted. Water is attracted to the cells' intracellular environment, which could cause a low degree of cellular swelling. After the cell had been rendered non-viable for several hours, larger intracellular constituents such as salts and proteins began to exit the cell and leak through the membrane proteins. This can be observed as cellular fragmentation and degrading. These properties cause physical changes in the appearance of the embryo which can be observed over time. However, the changes of healthy embryo growth and development, nor embryo death or decay can be observed in acute settings. Applying video motion magnification software to embryos allows one to see embryo development or embryo decay. This can be applied to embryos immediately prior to transfer to check embryo developmental competency before being transferred into the patient's uterus. On a practical level, the technology benefits the clinical embryologist because it enables a multi-embryo scan, is non-invasive and is compatible with standard video equipment.

In a pilot study, bovine oocytes were fertilized in vivo by a licensed veterinarian. The embryos are flushed from the donor and placed in holding media. Two-minute video recordings are captured on an inverted microscope at 150× magnification. Recorded videos are uploaded into Lambda Vue, a video motion magnification video scope. Measurements to document embryo change are obtained using ImageJ Software. Zona pellucida X axis diameter, zona pellucida Y axis diameter, mass X axis diameter, mass Y axis diameter, zona area, mass area, inner cell mass area, and rotational shift within the subzonal space are documented at 0, 15, 30, 45, 60, 75, 90, 105, 120 second time points. All recorded embryos are transferred into recipient animals as singletons. Currently, 35 second video clips at 10 fps are being captured, magnified and analyzed.

The data demonstrates that there are significant differences in embryo area and size during a short, two-minute time period, and video motion magnification is effective at depicting these changes. Pregnancy data is obtained by trans-rectal ultrasound 40 days post transfer.

In an initial study, 150 grade 1 and 2 blastocysts and morula were flushed from beef cattle from a licensed veterinarian. Two-minute video recordings were captured from each embryo with an Iolight® inverted microscope at 150× in standard culture in Vigro Holding Plus media. All embryos were transferred into eligible recipients. Videos were processed with Lambda Vue Video Motion Magnification Videoscope at 0.2-4 video frequency. Amplified videos were then assessed with ImageJ measuring tools to make a quantitative analysis at 15 second time intervals. The following measurements were assessed: Zona pellucida Y axis diameter, zona pelludica X axis diameter, mass Y-axis diameter, mass X-Axis diameter, zona pelludica area, mass area, observation of bulges on zona pellucida, observation of bulges on mass, sub-zonal space at 12 locations as generally depicted in FIGS. 2 and 3.

Changes were observed in all measured properties over time amongst individual embryos. Changes in the degree of shift of the mass within the zona pelludica (measurement of the sub-zonal space) and degree of physical change in the shape and structure of the inner cell mass demonstrates the largest degree of change were expressed as a percentage. These parameters were correlated to pregnancy outcomes to build deep learning algorithms to predict pre-implantation embryo developmental potential.

Regarding the animal sciences, in 2050 the global population is expected to reach 9.5 billion and it is projected the demand for animal derived protein will double, resulting in concerns for sustainability and food security. Current agricultural practices are already placing tremendous pressure on Earth's finite resources and are largely responsible for a vast proportion of greenhouse gas (GHG) emissions. Well managed cattle production can be advantageous to meeting food security and environmental goals, as beef and dairy is a nutrient-rich high quality protein and cattle are a robust animal, which can adapt to climate change, graze on pasture land generally unsuitable for crop production due to climate, soil and topographic limitations, produce fertilizer and convert forage into high quality protein. Modern cattle production practices have been successful in reducing the carbon footprint of cattle production, as methane output has declined 40% since 1980. Genetic selection through progressive breeding strategies can further reduce GHG emissions from cattle production though improving animal efficiency, improving the feed conversion ratio, reducing dry matter intake and reducing enteric methane production.

Methane ($CH_4$) is the major GHG emitted from ruminant production systems with $CH_4$ from enteric fermentation accounting for 12% to 17% of GHG emissions. Diet is a major contributing factor and the impact of roughage and concentrate diets on increasing the $CH_4$ emissions in ruminant systems is well known. Increasing cereal grains, starch content of small grain and corn, increasing legume composition and utilizing plant species containing secondary metabolites such as tannins or saponins that affect methanogenesis in the rumen are known to reduce daily $CH_4$ emissions in ruminant species. Effectiveness of feedlot programs implementing dietary improvements has improved the carbon footprint of beef production in Canada to as low as 17 kg carbon dioxide equivalents ($CO_{2e}$/kg) for feedlot finished beef as compared to grass-finished beef in Brazil which can emit 40 $CO_{2e}$/kg. Despite these advantages, grassland renovation is often not practical as many of these plant species are weak competitors with grasses and have a narrow climatic and geographic adaptation and increased grain supplementation is not affordable or sustainable. Therefore, the most practical and rapid mitigation procedure may be to reduce the per cow $CH_4$ emission through animal breeding and genetic selection for feed efficiency, as it is permanent and cumulative.

Genetic selection can reduce GHG emissions from beef and dairy cattle production system as genetic selection (1) enables increased production per animal which reduces the number of individual animals to produce the same amount of beef and dairy; (2) Lowers emission per unit of beef or dairy produced and (3) Reduces consumption of grain, concentrates, roughage, water and land. Embryo transfer (ET) and in vitro fertilization (IVF) can further perpetuate genetic traits of superior animals because they enable superior animals to have more genetic offspring in a single year than can be achieved in nature. Heritable phenotypes of interest to reduce GHG emissions from beef and dairy cattle include feed intake, rumen flora, milk fatty acid composition, residual feed intake and feed efficiency. Additionally, ARTs can help producers control the sex ratio to be favorable for sex most desirable for the operation (ex. dairies prefer females because they produce milk) and offer economic advantages such as decreased calving intervals, more consistent calf crop production and maximized product value. Due to these benefits, ET and IVF have become routine breeding strategies in livestock operations and approximately 2.5 million cattle embryos are transferred in North America each year.

To perform ET or IVF, superior female animals referred to as "donors" are stimulated with super-ovulatory hormones to produce an increased number of oocytes. The oocytes can be aspirated from the ovary by a veterinarian and fertilized in vitro or the animal can be artificially inseminated and fertilized embryos can be flushed from the uterus 6-7 days later. At this stage, the veterinarian or embryologists examines the embryos under a light microscope and assigns a grade based on visual morphological characteristics. At this point, high quality grade 1 & 2 embryos are transferred into recipients or frozen for use at a later date.

Unfortunately, success rates of ET and IVF are still very low. Conventional ET success rate is less than 65% and IVF success rates is less than 30% in cattle. While causes of failed pregnancy are multi-factorial and can stem from embryonic, maternal or environmental stressors, it is estimated that 20% of transferred embryos are already non-viable at time of transfer and will never result in pregnancy. Emerging technologies which are non-invasive and non-subjective to predict embryo health and sex can increase pregnancy outcomes to improve the efficiency of animal breeding systems and reduce negative environmental impacts to generate a more sustainable future.

Pregnancy rates and control of the sex ratio are valuable. Approximately $1200 USD is invested into each embryo transferred, regardless whether it establishes a pregnancy. With current pregnancy outcomes of less than 65% for conventional transfer and less than 30% successful for IVF, any technology to improve pregnancy outcomes offers significant savings to producers. Additionally, genetically superior animals with a sex advantageous for the specific production system offer increased value. ET coupled with the use of the present technology is the fastest way to change and improve the genetics in a herd and maximize producer profitability and environmental sustainability. A $1.5 billion initial market opportunity has been identified in North America to improve pregnancy outcomes of ET and IVF in cattle.

Videos of embryos were obtained and amplified using video motion magnification. Y axis diameter of the outer boundary or perimeter of the zona pellucida was measured using ImageJ software (National Institute of Health) and scaled to represent units in microns. Measurements were obtained at 5 second intervals from 0 to 35 seconds. Quantifiable changes in embryo diameter were observed, demonstrating morphokinetic changes in short observatory periods. Changes in embryo diameter occur independently on a per embryo basis.

Videos of embryos were obtained and amplified using video motion magnification. Y axis diameter of the cellular mass was measured using ImageJ software (National Institute of Health) and scaled to represent units in microns. Measurements were obtained at 5 second intervals from 0 to 35 seconds. Quantifiable changes in embryo mass diameter were observed, demonstrating morphokinetic changes in short observatory periods. These were observed visually as bulges, depressions and protrusions in the cellular mass over time. These changes infer predictive information pertaining to embryo health and viability.

Videos of embryos were obtained and amplified using video motion magnification. Area of the inner cell mass was obtained using measurement tools available from ImageJ software (National Institute of Health) and scaled to represent units in microns. Measurements were obtained at 5 second intervals from 0 to 35 seconds. Quantifiable changes in mass area were observed, demonstrating morphokinetic changes in short observatory periods. Measurements represent a 2D area of the visible mass. It was observed the cells were actively moving, likely due to mitosis and cellular divisions. At some points, it is likely individual cells overlapped making the 2D area appear to decrease. The present technology demonstrates active development or cellular decay and does not depend on additive or subtractive trends. These changes are evident of kinetic developmental properties to predict embryo health, viability, stress, and genetic characteristics.

The origin of the data processed by machine learning to develop a model for assessing and predicting future embryo capabilities/characteristics is video of pre-implantation embryos that are typically in the blastocyst or morula stage of development which occurs between about five to nine days, post fertilization. The embryos can be the product of either in vitro fertilization ("IVF") or in vivo fertilization (after which the embryos are flushed from the host). In this specification, references to "blastocyst" should be considered to include at least morula stage embryos.

The assessment is of the blastocyst's movement over a relatively short period of time. As an example, 30 seconds or less, but as much as 5 to 10 minutes. The video of this disclosure is real-time video, as compared to time-lapse video, which is known for use in embryo assessment. In this context, time-lapse video is taken over an extended period of time (usually hours, but more typically days) and is made-up of a series of consecutive still photos or "frames" that have substantial time-spacings (30 seconds or more, but typically minutes or hours) therebetween. As defined in Merriam Webster's Dictionary, time-lapse is "of, relating to, or constituting a motion picture taken at a speed slower than normal but usually projected at a normal speed so that a slow action (as the opening of a flower bud) appears to be speeded up." Heretofore, relatively short period, real-time video of an embryo has not been analyzed regarding short-term movements because none were visually detectable, including when using magnification as is typical for time-lapse embryo observation and evaluation.

In fact, as described herein, significant movement has been discovered to be occurring in the blastocyst. In accordance with the present disclosure, this movement is recorded in real-time video typically taken via a microscope using a magnification power (e.g., 150×) suitable for embryo observation. However, even under the magnification of a microscope, this recorded movement of the blastocyst is still not humanly perceptible. But knowing that the blastocyst's motion is recorded in the real-time video, even though not perceptible, the image data of the video is prepared for machine analysis.

As with all video, the presently disclosed real-time video clips comprise a series of consecutive, equal-time-spaced image frames which is usually referred to as frame speed. The blastocyst movement being recorded necessarily traverses a short distance, typically at a fast rate, and therefore for a short duration. Consequently, the frame speed utilized for these recordings should be of commensurate duration, and preferably faster. In at least one example, a frame speed of ten frames-per-second (10 fps) is utilized to capture the blastocyst movement. In practice, faster frame speeds have proven beneficial, particularly in training stages of the presently disclosed AI/ML analysis because the quick, short-distance movements made by the blastocyst are captured with greater accuracy and clarity. Conversely, as frame speed decreases and there are greater time gaps between consecutive frames, the blastocyst movement becomes less perceptible.

For present purposes, it is desirable that each instance of video-based image training data (and subsequently, video-based target image data to be analyzed using resulting so-trained models) be that of a relatively short, real-time video clip. For example, from around fifteen seconds up to several minutes long. It is not necessary that each clip be individually recorded; they can be excised out of a longer blastocyst video, but selected to correlate best to video image data that will be processed by the resulting model; therefore, utilizing training data clips of similar duration subsequently enables more accurate predictions therefrom.

Whether being prepared as training data or as target data to be analyzed by a so-trained model, preprocessing of the respective blastocyst image data sets of the different videos can include normalizing the "raw" image data sets to that of a "standard" blastocyst. Though various known methods can be used to accomplish such normalization, the desired end result is that the sets of video image data be able to be compared, one to the others, with less distortion and "noise". One example is to adjust one or more sets of blastocyst image data to the same "size" by scaling up (expanding) or scaling down (shrinking) the respective data sets to a "standard size" thereby facilitating their use for training or model-analysis.

In some instances, such "size" normalization will not be applied because the size of the blastocyst is to be measured. For instance, size can be predictive of blastocyst viability and/or gender. Relatedly, relative blastocyst size can also be a determining or desired differentiating factor amongst a group of co-fertilized blastocysts (multiple eggs fertilized at the same time and growing together in a sample dish) that are being model-assessed for viability and/or gender, and relative size is predictive, or at least can be used to rank the blastocysts within the group.

Another aspect of pre-processing that can be applied to the image data is motion amplification, also referred to as motion magnification. As described above, the distance over which blastocyst motion occurs is so small that it is not humanly visible, not even at typical microscope magnification power (e.g., ×150), but the motion is none-the-less highly predictive of blastocyst characteristics (e.g., viable, male, female) and capabilities (e.g., likelihood to produce pregnancy and/or full-term, live offspring). Therefore, motion magnification can be applied to provide several benefits.

An initial benefit of amplification is that it can make the blastocyst movement humanly perceptible. This is important because it renders the blastocyst movement more "real" to an operator who might otherwise be skeptical. The other is that certain blastocyst motion, if present, is directly predictive to a user. For instance, certain blastocyst movement(s) that are rendered visible by the amplification are predictive of viability versus non-viability, which is of paramount interest. As otherwise explained in greater detail in this specification, in the human and non-human (animal) setting, the avoidance of implanting a non-viable embryo in a recipient animal is highly desirable, with this being even more so in non-human applications directed toward the production of animals. Still further, the described methods for collecting the video information/data increases the practicality and feasibility of this product as it delivers faster results and shortens the time required to generate meaningful predictive data.

Figure 7:
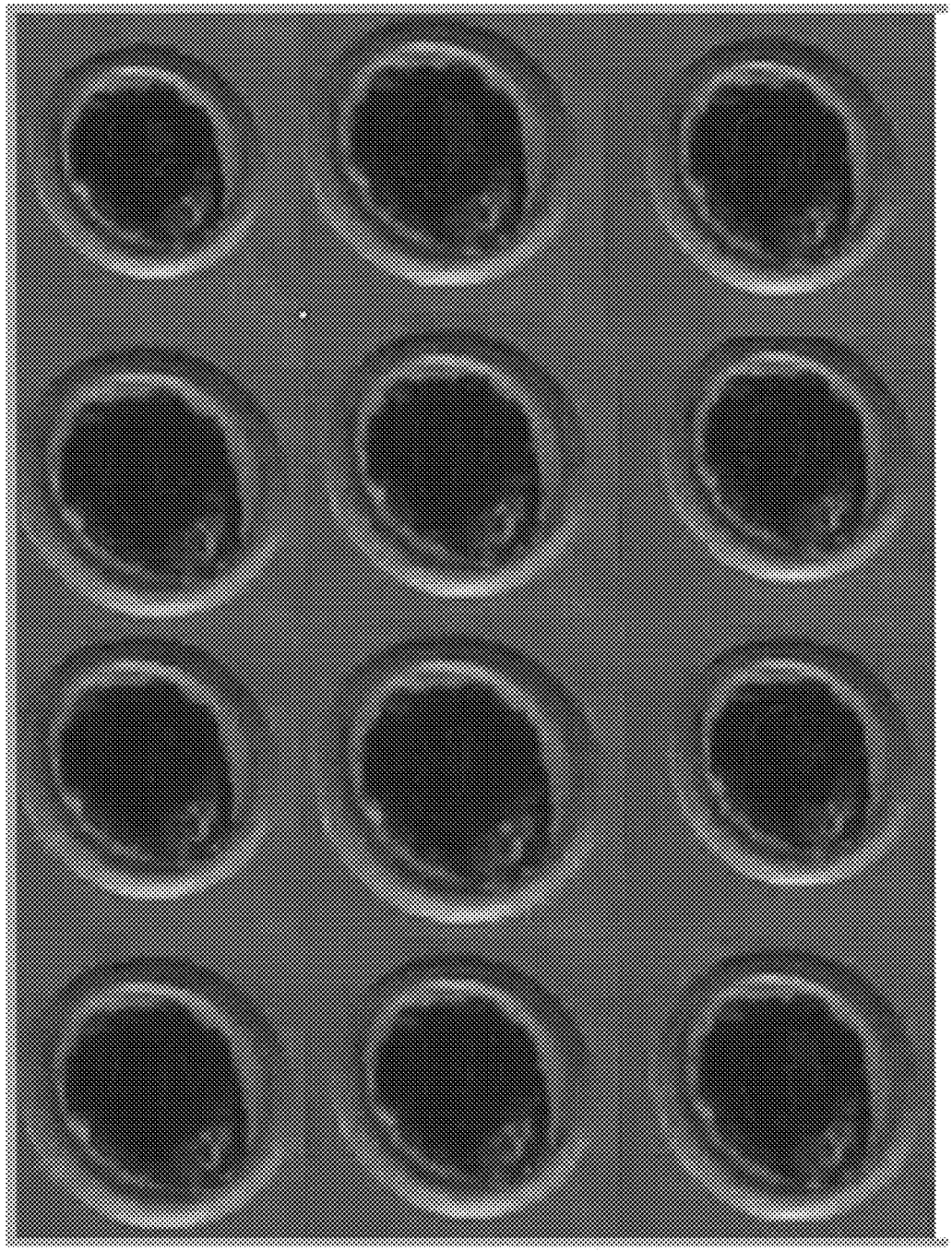
FIG. 7 depicts a series of 12 frames extracted from a video clip of a blastocyst at 150×magnification.
Figure 8:
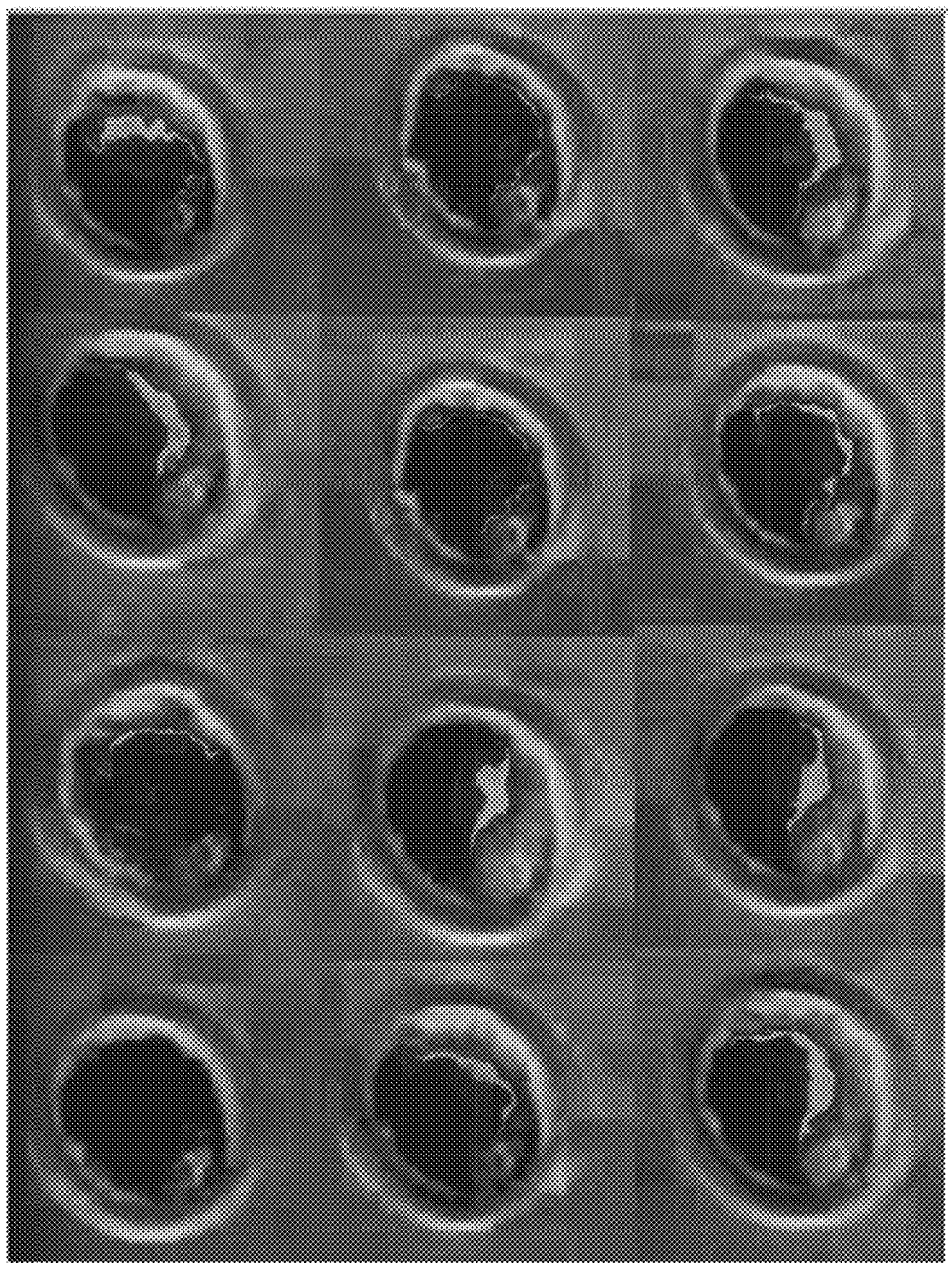
FIG. 8 depicts the same 12 frames of FIG. 7, but after motion magnification.

FIG. 7 depicts a series of 12 frames extracted from a video clip of a blastocyst (having a frame rate of 2 fps), without magnification (arranged left to right, top to bottom). Though it is known that blastocyst motion is occurring, it is not visible, even under the 150×magnification. However, FIG. 8 depicts the same 12 frames after motion magnification, and consecutive frames clearly depict motion in that the frames are progressively different, indicative and illustrative of the blastocyst's real-time motion.

Another benefit of motion amplification is that the amplified image data accentuates the motion characteristics being analyzed (via computer vision, digital image processing or otherwise) during the training and model development stage, or afterward during utilization of the resulting model for predictive purposes.

During the training process, the model can be trained to predict among other things, viability, likelihood to produce pregnancy, likelihood to result in a live birth, whether male or female, and the presence or absence of genetic anomalies and disease, such as diabetes, cancer and the like.

Video motion magnification can be used to evaluate acute responses to environmental stressors which provide insight to developmental and health outcomes. Understanding embryo homeostasis mechanisms through visualizing embryo response to variables can help optimize culture systems, medias, materials, nutrients, cellular metabolism, ambient environment and overall developmental competency. These can be useful to determine early prognosis of cancer, metabolic profile or genetic defects.

Cystic fibrosis (CF) is caused by a genetic mutation in the CFTR gene which regulates the chloride channel. It is a genetically recessive disease. Prospective parents can be screened to determine carrier status. The only way to determine CF is through pre-implantation genetic diagnosis of embryos (biopsy process). People having CF cannot regulate chloride transport; therefore, when chloride is added to the media containing the embryo, predictive motion is observed. The embryos which can "tolerate" the chloride are likely healthy and can process and metabolize it properly as they are void of the CFTR genetic mutation. The embryos that show an unfavorable response (such as rapid motion indicating stress) are determined to not process chloride properly and the technology disclosed herein provides a non-invasive means to diagnose cystic fibrosis.

More than 1,000 mutations in the CFTR gene have been identified in people with cystic fibrosis. Most of these mutations change single protein building blocks (amino acids) in the CFTR protein or delete a small amount of DNA from the CFTR gene. The most common mutation, called delta F508, is a deletion of one amino acid at position 508 in the CFTR protein These principles apply to identify many genetic and metabolic diseases. Glucose in the media predicts diabetes. Potassium detection in the media predicts Hyperkalemic Periodic Paralysis in horses and others.

Visualizing embryo responses enables the comparison and understanding of embryo rate of growth and morphology-kinetic activity or degradation.

The present technology facilitates non-invasive embryo sex selection. There is scientific evidence indicating that male embryos develop faster than female embryos. This is observed by total cell count at the blastocyst stage of development. The data is predominantly anecdotal because it is difficult to count cells non-invasively without harming the embryo. However, in order for there to be greater male cell count over a predetermined period of time, the number of cells in male embryos must multiply at a faster rate. Video motion magnification can be used to detect and determine embryo rate of growth to forecast cell count to non-invasively predict embryo sex.

The resulting trained model is applicable for predicting such things as viability, likelihood to produce pregnancy, likelihood to result in a live birth, whether male or female, and the presence or absence of genetic anomalies. These predictions are made from processing image data from a video of a blastocyst generally consistent with the videos upon which the model was trained. Typically, the video of the blastocyst to be analyzed is taken in the "field," which is considered to be wherever the blastocyst is evaluated for implantation or preservation. In this context, "field" when referring to animals can be a veterinarian clinic, barn, stock trailer and/or outdoors, for example. When considering humans, "field" typically refers to a fertility clinic and the like. Therefore, to avoid the need to transmit the video (which can be a data file of substantial size) to a remote analysis site, the model can be located on a local processor (computer, tablet, smart phone and the like) where the desired predictions are made. In this configuration, however, control by the developer of the model is lost. Alternatively, the data file can be transmitted to the developer's remote site where the video file is processed, and predictions transmitted back to the user in the field.

In practice, in the field where blastocysts are collected, it is common for a plurality of blastocysts to be suspended in nutritional media in a single, disposable receptacle, petri dishes, organ culture dishes and multi-well plates. Accordingly, a single video can be taken and processed regarding each of the blastocysts for the characteristics for which the model has been trained. An important aspect of the receptacle is that it has a transparent, substantially flat floor. An inverted microscope is utilized to record a substantially distortion-free video of the blastocyst(s) from below the receptacle, through its clear, flat bottom surface. This creates a "goggle effect" and reduces noise in the sample from wave refraction caused by a rippling upper surface of the liquid media. Exemplarily, the Iolight® brand compact inverted microscope has been utilized to record the original video of the blastocyst(s). The magnification power is one-hundred and fifty times (150×), the frame speed is 10 fps, the pixel density is 2592 x 1944 and the microscope connects to smartphones and tablets for making and/or sharing produced videos.

The relative strength of a predicted characteristic among a group of blastocysts can also be computed and delivered. As most of the characteristics that are predictable by the model are based on characteristics of the videoed motion, the strength (score) of most of those characteristics can be assessed based on the relative amplitude of the predictive motion between the relevant blastocysts. Still further, selective amplification of certain motion characteristics can focus the predictions of the applied model.

As an example, in the instance of a dairy operation, ten blastocysts have been flushed from a donor cow and deposited into a petri dish. There are only five available recipient cows, so the technician wishes to identify the five most viable, female blastocysts. These predictions can be calculated using the trained model and communicated back to the technician visually, or otherwise. In this way the technician can transfer the five blastocysts most likely to produce a female calf as desired by a dairy operation. Similar other examples can be characteristically appropriate for both other animal production beneficial for non-dairy operations, and for selective human reproduction choices and decisions.

What is claimed:

1. A method for assessing a characteristic of an embryo by processing real-time video image data of the embryo, the method comprising:

obtaining real-time video of a target embryo having frame speed at least as fast as two frames per second, said real-time video comprising image data representing micro-motions of the target embryo; and processing said image data using a trained machine learning model and thereby assessing a characteristic of the target embryo.

2. The method of claim 1, wherein said real-time video is a continuous recording having a real-time duration of five minutes or less and the entirety of which has been taken immediately prior to the embryo's transfer into a recipient.

3. The method of claim 1, wherein said real-time video is a continuous recording capturing micro-motions of the embryo and having a real-time duration of two minutes.

4. The method of claim 3, wherein said real-time video of the target embryo has a frame speed at least as fast as ten frames per second.

5. The method of claim 1, wherein said real-time video is a continuous recording having a real-time duration of thirty seconds.

6. The method of claim 1, wherein the assessment further comprises predicting a likelihood the target embryo will produce pregnancy upon transfer into a recipient.

7. The method of claim 1, wherein the assessment further comprises predicting a likelihood the target embryo will produce a specific sex offspring.

8. The method of claim 1, wherein the assessment further comprises predicting at least one of: (1) a likelihood the target embryo embodies a genetic anomaly; (2) a likelihood the target embryo will perpetuate desired traits in produced offspring; and (3) a likelihood the target embryo will produce undesired characteristics in produced offspring.

9. The method of claim 1, wherein said model is trained utilizing machine learning and correlated pregnancy data to determine viability of the target embryo.

10. The method of claim 1, wherein the image data simultaneously represents a plurality of target embryos.

11. The method of claim 10, further comprising: processing image data representing each of the plurality of target embryos utilizing the model and thereby scoring each target embryo.

12. The method of claim 1, wherein processing the image data further comprises amplifying at least a portion of the image data representing micro-motion of the target embryo.

13. The method of claim 12, wherein the amplification of image data is made utilizing video magnification.

14. A system comprising:
    one or more processors; and
    a computer-readable medium comprising instructions stored therein, which when executed by the one or more processors, cause the one or more processors to:
    assess an embryo characteristic by processing video image data of the embryo, said assessment comprising:
        receiving real-time video of a target embryo having frame speed at least as fast as two frames per second, said real-time video comprising image data representing micro-motions of the target embryo; and
        processing said image data using a trained machine learning model and thereby assessing a characteristic of the target embryo.

15. The system of claim 14, wherein said real-time video is a continuous recording having a real-time duration of five minutes and the entirety of which has been taken immediately prior to the embryo's transfer into a recipient.

16. The system of claim 14, wherein said real-time video is a continuous recording capturing micro-motions of the embryo and having a real-time duration of two minutes.

17. The system of claim 16, wherein said real-time video of the target embryo has a frame speed at least as fast as ten frames per second.

18. The system of claim 14, wherein said real-time video is a continuous recording having a real-time duration of thirty seconds.

19. The system of claim 14, wherein the assessment further comprises predicting a likelihood the target embryo will produce pregnancy upon transfer into a recipient.

20. The system of claim 14, wherein the assessment further comprises predicting a likelihood the target embryo will produce a specific sex offspring.

21. The system of claim 14, wherein the assessment further comprises predicting at least one of: (1) a likelihood the target embryo embodies a genetic anomaly; (2) a likelihood the target embryo will perpetuate desired traits in produced offspring;

and (3) a likelihood the target embryo will produce undesired characteristics in produced offspring.

22. The system of claim 14, wherein said model is trained utilizing machine learning and correlated pregnancy data to determine viability of the target embryo.

23. The system of claim 14, wherein the image data simultaneously represents a plurality of target embryos.

24. The system of claim 23, further comprising: processing image data representing each of the plurality of target embryos utilizing the model and thereby scoring each target embryo.

25. The system of claim 14, wherein processing the image data further comprises amplifying at least a portion of the image data representing micro-motion of the target embryo.

26. A method for assessing a characteristic of an embryo by processing real-time video image data of the embryo, the method comprising:
    obtaining a real-time video of a target embryo having a continuous real-time recording duration of ten minutes or less, said real-time video comprising image data representing micro-motions of the target embryo; and
    processing said image data using a trained machine learning model and thereby assessing a characteristic of the target embryo.

27. The method of claim 26, wherein said real-time video has a continuous real-time recording duration of five minutes and the entirety of which has been taken immediately prior to the embryo's transfer into a recipient.

28. The method of claim 26, wherein said real-time video has a continuous real-time recording duration of 30 seconds.

29. A non-transitory computer-readable storage medium comprising computer-readable instructions, which when executed by a computing system, cause the computing system to process video image data of an embryo comprising:
    obtaining a real-time video of a target embryo having a continuous real-time recording duration of 30 seconds, said real-time video comprising image data representing micro-motions of the target embryo; and
    processing said image data using a trained machine learning model and thereby assessing a characteristic of the target embryo.

30. The storage medium of claim 29, wherein the assessment further comprises predicting a likelihood the target embryo will produce a specific sex offspring.

* * * * *